(12) United States Patent
Smirnov

(10) Patent No.: US 10,952,612 B2
(45) Date of Patent: Mar. 23, 2021

(54) PASSIVE SENSORS AND RELATED STRUCTURES FOR IMPLANTABLE BIOMEDICAL DEVICES

(71) Applicant: Yuri Smirnov, Eagan, MN (US)

(72) Inventor: Yuri Smirnov, Eagan, MN (US)

(73) Assignee: Geissler Companies, LLC, Minneapolis, MN (US)

(*) Notice: Subject to any disclaimer, the term of this patent is extended or adjusted under 35 U.S.C. 154(b) by 656 days.

(21) Appl. No.: 15/667,375

(22) Filed: Aug. 2, 2017

(65) Prior Publication Data

US 2018/0036115 A1 Feb. 8, 2018

Related U.S. Application Data

(60) Provisional application No. 62/370,563, filed on Aug. 3, 2016.

(51) Int. Cl.
*A61B 5/00* (2006.01)
*A61B 5/024* (2006.01)
(Continued)

(52) U.S. Cl.
CPC ........ *A61B 5/0031* (2013.01); *A61B 5/02444* (2013.01); *A61B 5/1451* (2013.01); *A61B 5/4312* (2013.01); *A61B 5/6869* (2013.01); *A61B 5/6876* (2013.01); *A61F 2/12* (2013.01); *A61F 2/2472* (2013.01); *G06F 19/3468* (2013.01); *G06K 7/10366* (2013.01); *G06K 19/0723* (2013.01); *G16H 40/67* (2018.01); *G16H 50/20* (2018.01); *H04Q 9/00* (2013.01);
(Continued)

(58) Field of Classification Search
CPC ........... A61F 2/12; A61B 5/0031; A61B 5/68; A61B 5/6867; G16H 40/67
See application file for complete search history.

(56) References Cited

U.S. PATENT DOCUMENTS

| 8,248,232 B2 | 8/2012 | Stevenson et al. |
| 2008/0048855 A1 | 2/2008 | Berger |

(Continued)

FOREIGN PATENT DOCUMENTS

WO 2018026945 2/2018

OTHER PUBLICATIONS

"International Application Serial No. PCT/US2017/045142, International Search Report dated Nov. 1, 2017", 10 pgs.
(Continued)

*Primary Examiner* — William H Matthews
(74) *Attorney, Agent, or Firm* — Cozen O'Connor

(57) ABSTRACT

A biomedical implant includes a wall enclosing at least a portion of the implant. The wall includes a first stratum and a second stratum conformal with the first stratum. An interlayer is provided between the first and the second strata, and includes a structure that produces capillary pressure in an infiltrating fluid in response to rupture of the first stratum or the second stratum resulting in entry of the infiltrating fluid into the interlayer. A detector is exposed to the interlayer and configured to detect a presence, if any, of the infiltrating fluid and output a detection state indicator. A communication circuit is communicatively coupled to the detector and configured to communicate the detection state indicator to a reader external to the patient.

12 Claims, 6 Drawing Sheets

(51) Int. Cl.
    *A61B 5/145*     (2006.01)
    *A61F 2/24*     (2006.01)
    *G16H 50/20*     (2018.01)
    *G16H 40/67*     (2018.01)
    *A61F 2/12*     (2006.01)
    *G06F 19/00*     (2018.01)
    *G06K 7/10*     (2006.01)
    *G06K 19/07*     (2006.01)
    *H04Q 9/00*     (2006.01)
    *A61B 5/11*     (2006.01)

(52) U.S. Cl.
    CPC ..... *A61B 5/1108* (2013.01); *A61B 2560/0219* (2013.01); *A61B 2562/029* (2013.01); *A61B 2562/0219* (2013.01); *A61B 2562/0247* (2013.01); *A61B 2562/08* (2013.01); *A61F 2250/0002* (2013.01); *A61F 2250/008* (2013.01); *A61F 2250/0085* (2013.01); *A61F 2250/0096* (2013.01); *G06K 19/0709* (2013.01); *G06K 19/0716* (2013.01); *H04Q 2209/47* (2013.01); *H04Q 2209/886* (2013.01)

(56) References Cited

U.S. PATENT DOCUMENTS

| | | |
|---|---|---|
| 2008/0275327 A1 | 11/2008 | Faarbaek et al. |
| 2009/0012372 A1* | 1/2009 | Burnett ............... A61B 5/076 600/300 |
| 2014/0191026 A1 | 7/2014 | Simpson et al. |
| 2016/0022144 A1 | 1/2016 | Hansen |

OTHER PUBLICATIONS

"International Application Serial No. PCT/US2017/045142, Written Opinion dated Nov. 1, 2017", 7 pgs.

* cited by examiner

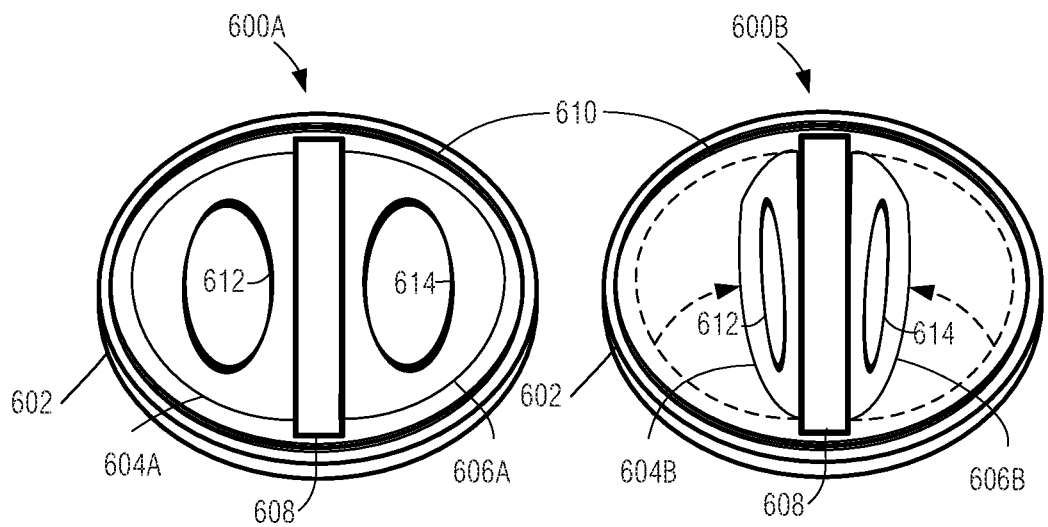
FIG. 6A  FIG. 6B
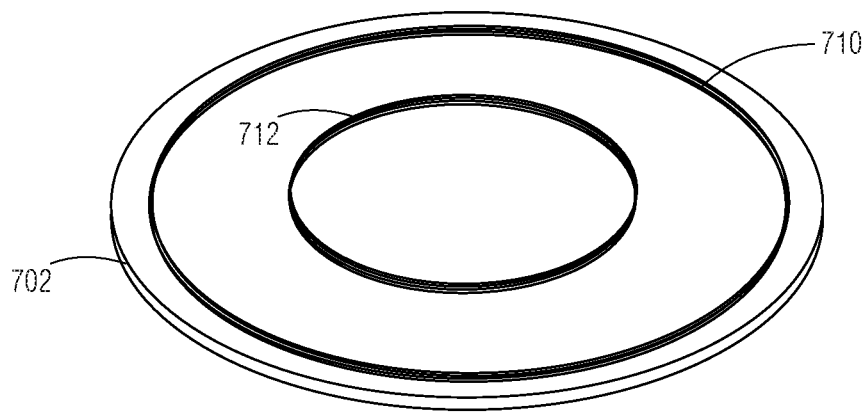
FIG. 7

US 10,952,612 B2

PASSIVE SENSORS AND RELATED STRUCTURES FOR IMPLANTABLE BIOMEDICAL DEVICES

PRIORITY

This application claims the benefit of priority of U.S. Patent Application Ser. No. 62/370,563, filed on Aug. 3, 2016, which is hereby incorporated by reference herein.

TECHNICAL FIELD

Embodiments described herein generally relate to testing and measurement. Some embodiments are more particularly directed to testing for structural and functional integrity of implantable biomedical devices.

BACKGROUND

Implantable biomedical devices, such as breast implants, artificial heart valves, and the like, have achieved a high level of reliability over the years. Nonetheless, structural or functional failure can occur, risking the well-being of the patient. For example, cosmetic implants may rupture, and mechanisms may break due to material failure, wear and tear, manufacturing defect, or an applied force.

Detection of such failures is not always simple or straightforward. For example, a breast implant may experience a very small tear, and may exchange fluids with the body, maintaining its shape for days, weeks, or longer. As another example, a heart valve may experience a gradual degradation in performance without exhibiting clear symptoms that may be felt by the patient. In these types of cases, even if a patient suspects a possible problem with an implanted device, conventional clinical tests or evaluations of potential problems tend to be costly, time-consuming, and sometimes invasive. Practical solutions are needed for detecting failures of implanted devices.

BRIEF DESCRIPTION OF THE DRAWINGS

In the drawings, which are not necessarily drawn to scale, like numerals may describe similar components in different views. Like numerals having different letter suffixes may represent different instances of similar components. Some embodiments are illustrated by way of example, and not limitation, in the figures of the accompanying drawings.

FIGS. 6A and 6B are diagrams illustrating an example application of a passive motion sensor, such as the sensor of FIG. 5A, to monitor the operation of an artificial heart valve according to an illustrative embodiment.

FIG. 7 is a diagram illustrating another example application of a passive motion sensor, such as the sensor of FIG. 5A, where the sensor is incorporated in a diaphragm structure according to an illustrative embodiment.

DETAILED DESCRIPTION

Aspects of the embodiments are directed to detection of various failure modes of implantable biomedical devices. One such aspect is directed to an implant having a multi-layered wall structure with a sensor and communications arrangement that facilitates detection of a rupture of a wall layer, and reliably providing that information to a reader.

Figure 1:
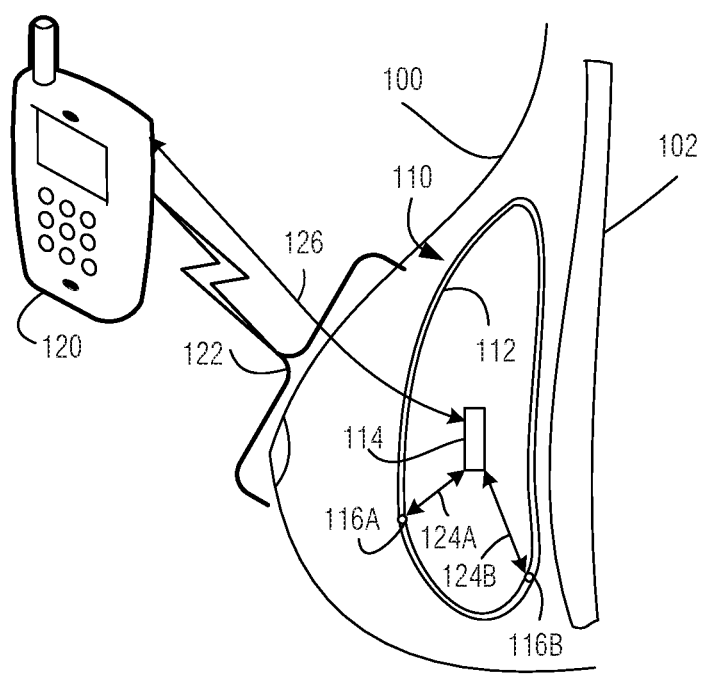
FIG. 1 is a diagram illustrating an example of a biomedical implant representing various embodiments.

FIG. 1 is a diagram illustrating an example of a biomedical implant representing various embodiments. In the present example, the biomedical implant is a breast implant 110 for patient 100. It will be understood that the principles described below are applicable to a variety of other types of implantable devices. As depicted, implant 110 is positioned in the breast of patient 100 proximate to muscle tissue 102.

Implant 110 has a wall 112 enclosing at least a portion of the implant. As shown, wall 112 is enclosing the entire implant. In the embodiments depicted, wall 112 is an exterior wall of implant 110; in other embodiments, wall 112 may be further enclosed by an exterior wall (not shown in these examples). The features of wall 112, which will be described in greater detail below, may be equally applicable for flexible walls, as is the case in the present example of a breast implant 110, and for more rigid walls, as may be the case with other types of implants.

Figure 2:
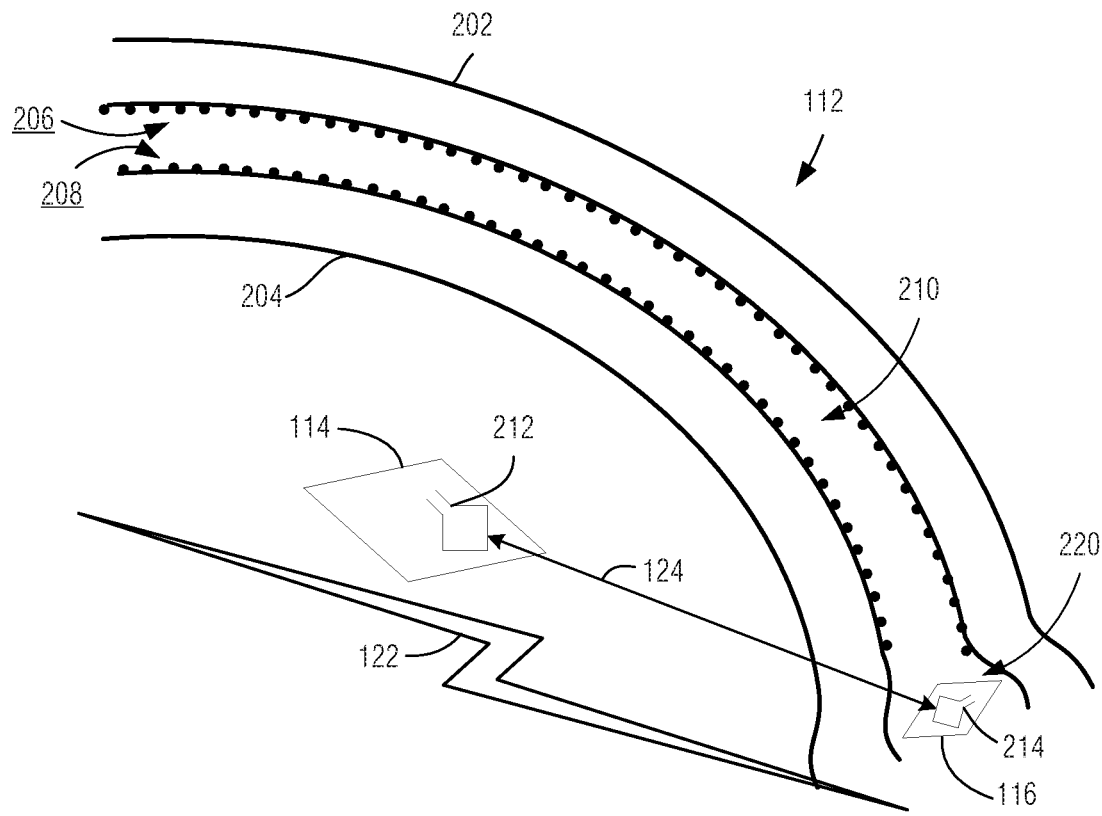
FIG. 2 is a schematic diagram illustrating portions of the biomedical implant of FIG. 1 in greater detail according to related embodiments.

According to some embodiments, wall 112 includes multiple layers, or strata, as well as infiltration sensors 116A, 116B (collectively, sensors 116) positioned within wall 112 and exposed to the interlayer between the strata. FIG. 2 is a schematic diagram illustrating a portion of wall 112, and sensors 116 in greater detail. Outer stratum 202 and inner stratum 204 may each be formed from a suitable, biocompatible, polymeric film, or sheet material. Strata 202 and 204 are conformal with one another, though in the diagram of FIG. 2 they are shown in a more spaced relationship for the sake of clarity of illustration.

Outer stratum 202 includes an interior surface 206, whereas inner stratum 204 includes an outer surface 208. Interlayer 210 is between surfaces 206 and 208, and includes a structure that utilizes surface tension to propel infiltrating fluid through interlayer 210 due to cohesive and adhesive forces between molecules of fluid and the surfaces 206, 208 of inner stratum 202 and outer stratum 204, respectively. The infiltrating fluid may be introduced to interlayer 210 as a consequence of the rupture of one or both strata 202, 204.

In one type of embodiment, as depicted in FIG. 2, one or both surfaces 206, 208 has a surface property that, when conforming to the other surface, forms channels, such as capillary channels, that produce the capillary action. In another type of embodiment, interlayer 210 is filled with an absorbent (e.g., sponge-like) material that produces the capillary action.

Detector 116 is exposed to interlayer 210. It may be situated entirely in interlayer 210, or otherwise fluidly coupled to interlayer 210. As depicted, detector 116 resides in a widened portion 220 that expands and conforms to accommodate detector 116.

Detector 116 is configured to detect a presence, if any, of the infiltrating fluid and output a detection state indicator. Detector 116 may include a suitable sensor that is sensitive to the infiltrating fluid. Detector 116 may also include a data communicator portion, such as a low-power transmitter, Detector 116 is communicatively coupled with a communication circuit 114 that is constructed to communicate a detection state indicator to a reader 120 that is external to the patient. In one example embodiment, as depicted in FIG. 1, the communication circuit 114 is a physically separate device from detectors 116A, 116B, and may be situated elsewhere in implant 110, such as in the interior of the breast implant 110. In an embodiment, communication circuit 114 is situated inside the interior of breast implant 110, on the back side of implant 110 towards the side nearest muscle tissue 102. In this type of embodiment, short-range wireless connectivity 124A, 124B may be provided between detectors 116 and communication circuit 114 via a transmitter circuit provided as part of each detector 116.

Communication circuit 114 includes a transceiver constructed to conduct trans-patient communications 126 with reader 120. Trans-patient communication 126 in the present context has a longer communication range than short-range wireless connectivity 124A, 124B. The longer communication range of the trans-patient communication 126 is comparative to the short-range wireless connectivity 124A, 124B, with the former having a longer range than the latter. In the present context, the terms "longer communication range" and "short-range wireless connectivity" are therefore not comparative, and not absolute terms of degree.

The short-range wireless connectivity may utilize a different carrier frequency than the trans-patient communication. Also, their relative electromagnetic field strengths, and the current densities in the respective transmission antennas may be substantially different.

In an embodiment, communication circuit 114 is incorporated as part of a radio-frequency identification (RFID) tag. In a related embodiment, detector 116 includes an RFID tag as well. In another related embodiment, the RFID tags of communication circuit 114 or detector 116 are passive RFID tags, meaning that they capture energy from RFID interrogation signal 122 sent from reader 120, and use that captured energy in order to perform their functionality. In certain passive-tag embodiments, the RFID tags do not have an independent energy store such as a battery, that would otherwise enable the tags to function independently from the captured energy of the RFID interrogation signal 122.

In one example configuration, the RFID tags from both, the communication circuit 114, and detector 116, are configured to utilize the captured energy to perform their respective operations. In this type of embodiment, even though detector 116 receives interrogation signal 122, its transmitter may lack the ability to generate a transmission field strength to report data directly to reader 120; hence, the communication circuit 114 is utilized as a data relay. Notably, in other embodiments, detector 116 may communicate data directly to reader 120.

In a related embodiment, communication circuit 114 is integrated with a data storage device, such as a non-volatile memory, that is configured to store some of the data received from detector 116, such as the most recent N measurements (with N being a predefined quantity), or a computed statistical value derived from prior measurements (e.g., running average, etc.). In a related embodiment, communication circuit 114 may also be integrated with a data processor that may execute certain decision logic to assess, based on past and present data from detector 116, whether a failure of wall 112 is probable.

Turning again to FIG. 2, an RFID embodiment is depicted in greater detail. Communication circuit 114 is depicted with relatively larger antenna 212, and detector 116 is depicted with relatively smaller antenna 214. In this example, relatively smaller antenna 214 is size constrained due to the positioning of detector 116 in fluid coupling to interlayer 210. The size-constrained smaller antenna 214 has less gain at the carrier frequencies than the relatively larger antenna 212; accordingly, a higher current density in the transmitter circuit and antenna would generally be needed to achieve an equivalent radiated field strength than the larger antenna 212. In an implantation site, the higher current density may cause undesirable effects, such as localized heating of the implant or surrounding tissue. Accordingly, in some embodiments the field strength of the signaling transmitted from detector 116 is lower, by design, than the field strength of the signaling transmitted from communication circuit 114.

Figure 3A:
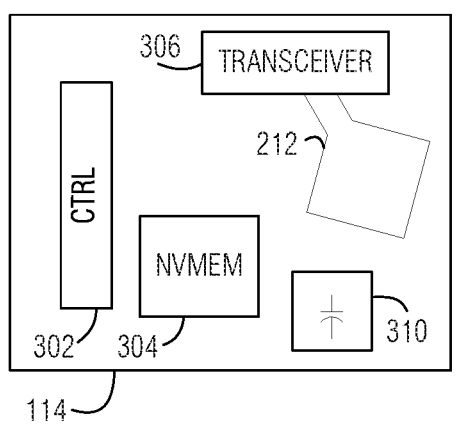
FIGS. 3A-3B are block diagrams illustrating some of the components of a communication circuit and of a detector, respectively, according to example embodiments.

FIG. 3A is a block diagram illustrating some of the components of communication circuit 114 according to an example embodiment. As depicted, communication circuit 114 includes controller 302, non-volatile memory 304, RF transceiver 306 with antenna 212, and captured-energy storage circuit 310. These components may be encapsulated by an encapsulating structure formed from a biocompatible material.

Controller 302 may include a processor circuit and firmware data store that contains instructions executable on the processor circuit according to one type of embodiment. In another embodiment, controller 302 may have hard-wired logic circuitry rather than instruction-executing circuitry. In still another embodiment, controller 302 may have some combination of instruction-executing, and hardwired, circuitry. Controller 302 is generally configured to coordinate operation of the other components. In some embodiments, controller 302 includes data-processing and decision logic to control operation in response to variable circumstances. Non-volatile memory may include a flash memory device, or other suitable data-storage technology, for storing data received from detector device(s) 116.

Transceiver 306 includes circuitry for receiving an interrogation signal 122 from the reader 120, for receiving data from detector(s) 116, and for transmitting the data to reader 120, via antenna 212. One or more frequency bands may be utilized for the various communications.

Captured-energy storage circuit 310 is configured to condition and store the energy captured from the interrogation signal, and to supply that energy for the other components. Captured-energy storage circuit 310 may include such components as a rectifier, voltage converter (e.g., charge pump), charge-storage device such as a suitable capacitor, voltage regulator, and the like.

Figure 3B:
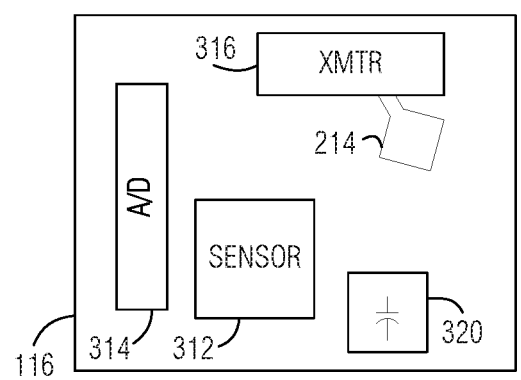

FIG. 3B is a block diagram illustrating detector 116 in greater detail according to some embodiments. Sensor 312 includes a suitable sensing technology to detect the presence of infiltrating fluid in interlayer 210. Examples (without limitation) include a conductivity sensor, a chemical sensor, a viscosity sensor, and the like. Notably, the infiltrating fluid may be interstitial fluid or other bodily fluid, or it may be fluid from the interior of the implant 110, such as silicone, saline, or the like. Analog-to-digital (A/D) converter circuit 314 is constructed with components such as filtering (e.g., low-pass, bandpass, time-domain filtering, tracking filtering), a sampling circuit, a quantizer, and the like, to produce a digital representation of the output of sensor 312. Transmitter 316 includes circuitry for sending the data via antenna 214 to a recipient, such as communication circuit 114, or reader 120. Captured-energy storage circuit 320 is similar in principle to captured-energy storage circuit 310 described above, though the size and energy utilization of detector 116 is generally expected to be less than that of communication circuit 114. At least a portion of the components of detector 116 (e.g., the A/D converter circuit 314, transmitter 316, captured-energy storage circuit 320) may be encapsulated by an encapsulation structure formed from a biocompatible material. Sensor 312 may be encapsulated fully or partially, depending on the sensing technology and the need to expose sensor 312 to the surrounding environment.

Figure 4:
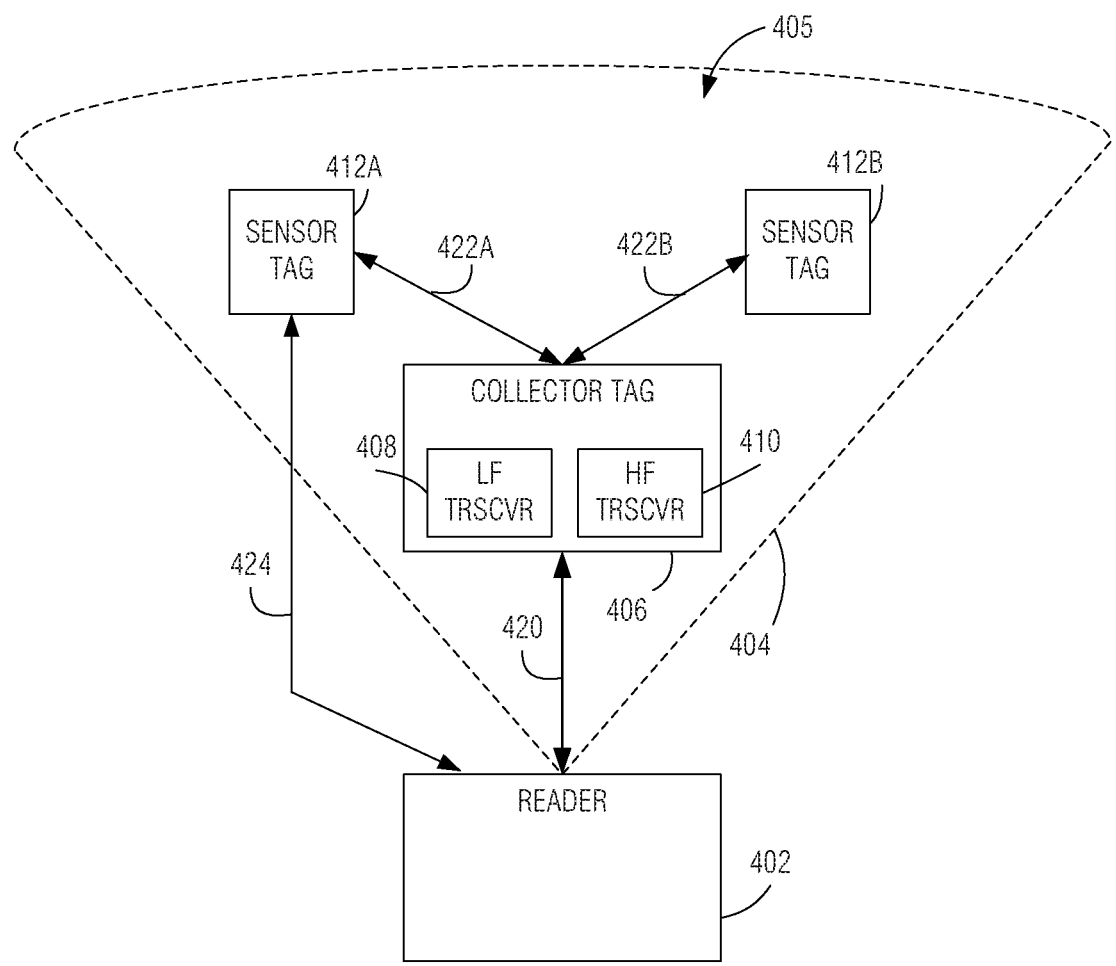
FIG. 4 is a diagram illustrating the operation of an RFID-based distributed sensor and collector-tag system according to an embodiment.

FIG. 4 is a diagram illustrating the operation of an RFID-based distributed sensor and collector-tag system according to an embodiment. RFID reader 402 is configured to transmit an interrogation signal 404 that energizes passive RFID tags within activation zone 405. Among the RFID tags in activation zone are collector tag 406, and sensor tags 412A and 412B.

Sensor tags 412A and 412B each include a sensing transducer and RFID tag circuitry configured to transmit data collected by the sensing transducer. In response to interrogation signal 404, sensor tags 412A and 412B store energy supplied by the interrogation signal, power up using the stored energy, take their respective sensor measurements, and transmit the collected data via respective communications 422A and 422B. Communications 422A and 422B may be in a high-frequency band, such as an ultra-high frequency (UHF) band, for example, to provide more efficient use of the small-size antennas of the sensor tags 412A, 412B. Alternatively, communications 422A and 422B may use a lower frequency band, such as a very-high frequency (VHF) band, a high-frequency (HF) band, or a low frequency (LF) band, to provide optimal RF wave propagation through a lossy medium such as the body, for example.

In another related type of embodiment, higher-frequency harmonics of the carrier frequency (and sidebands, if any) are selected by the reader for use in receiving data from collector tag 406 or sensor tags 412A, 412B. In a related embodiment, the selection of higher-order harmonics is made dynamically, such as in response to noisy RF environments.

Communications 422A or 422B may reach reader 402 with sufficient signal strength to facilitate effective communication of data to the reader. According to various embodiments, the reader may receive and store the data, or it may ignore the data directly from the sensor tags 412A, 412B.

In a related embodiment, one or more of the sensor tags may transmit its data via a different frequency band than the one used for communications 422A, 422B. As depicted, transmission 424 may have a frequency band that is better suited for transmission through the surrounding medium than communications 422A, 422B. In another related embodiment, sensor tags 412A, 412B include decision logic to select whether or not to make transmission 424. This decision may be based on an amount of energy available from the received interrogation signal, for example, where higher energy levels (e.g., in excess of a defined threshold) result in selective transmission of signal 424 for reception by reader 402.

Collector tag 406 has low-frequency transceiver 408, and high-frequency transceiver 410. According to some embodiments, various circumstances cause collector tag 406 to select whether to use one of these transceivers, or the other, for communications 420 with reader 402, or for communications 422A, 422B with sensor tags 412A, 412B. For example, collector tag 406 may determine an optimal energy management strategy for a given transmission based on the received strength of received signal from reader 402, and on the amount of data to be transmitted in a given communication session (e.g., in excess of a defined threshold). Thus, for instance, in the presence of a strong data signal from reader 402, and in response to a request from reader 402 for a relatively large amount of data, collector tag 406 may select high-frequency transceiver 410, which would enable collector tag 406 to transmit the data in a relatively shorter period of time than it could using low-frequency transceiver 408. The shorter-duration transmission may use less overall energy than a longer-duration transmission. In this example, the strong data signal from reader 402 may be used as an indicator that the signal from high-frequency transceiver 410 (which is generally less effective for transcutaneous transmission than the signal from low-frequency transceiver 408) has a high likelihood of being received by reader 402.

Collector tag 406 may also include non-volatile memory (not shown) for storing previous sensor measurements, and a data processor (also not shown) for computing various statistics on the collected sensor data. In one embodiment, collector tag 406 aggregates sensor data from sensor tags 412A and 412B before sending the data to reader 402. Aggregation may involve computing an average value, a differential value, a maximum or minimum value, or some other computationally-derived value based on a plurality of measurements from a plurality of sensor tags 412. Accordingly, data communications may be optimized by reducing the amount of raw sensor data from each individual sensor tag 412 that may otherwise need to be sent to reader 402 if the data from each individual sensor tag 412 were simply repeated, or relayed, by collector tag 406.

In a related aspect of the invention, one or both sensor tags 412A, 412B operate in conjunction with collector tag 406, reader 402, or both, to render a measurement. For example, in the case of a fluid-infiltration sensor arrangement, the principle of frequency-dependent signal dissipation may be utilized. Accordingly, the presence of fluid having some conductivity, such as blood, interstitial fluid, saline or silicone-based fluids, or the like, very close to the RF radiating element of each sensor tag 412A, 412B, may tend to attenuate RF transmissions from sensor tag 412A, 412B. Moreover, higher-frequency signals tend to be attenuated to a greater degree than lower-frequency signals. In an embodiment that utilizes these principles, sensor tag 412A, 412B transmits a sense-stimulation signal for reception by collector tag 406 or reader 402, which includes a relatively lower-frequency component, and a relatively higher-frequency component. In an example, the sense-stimulation signal is a data signal sent using frequency-shift keying that frequency-modulates the signal between a lower-frequency carrier wave, and a higher-frequency carrier wave according to a stream of data. The stream of data may be a fixed data item, such as an ID number of the sensor tag 412, or it may be a variable value representing some other sensed parameter, for example. The collector tag 406 or reader 402 receiving the sense-stimulation signal may compare the difference in received signal amplitude between the low-frequency component and the high-frequency component at a first time instance, against the difference in received signal amplitude between the low-frequency component and the high-frequency component at a second time instance, and test for any variation in the difference measures from one time instance to another. This variation may be indicative of fluid infiltration if, for example, the difference measure increased from the first time instance to the second time instance as a result of greater attenuation of the high-frequency component in the immediate presence of infiltrating fluid around sensor tag 412A, 412B.

Figure 5A:
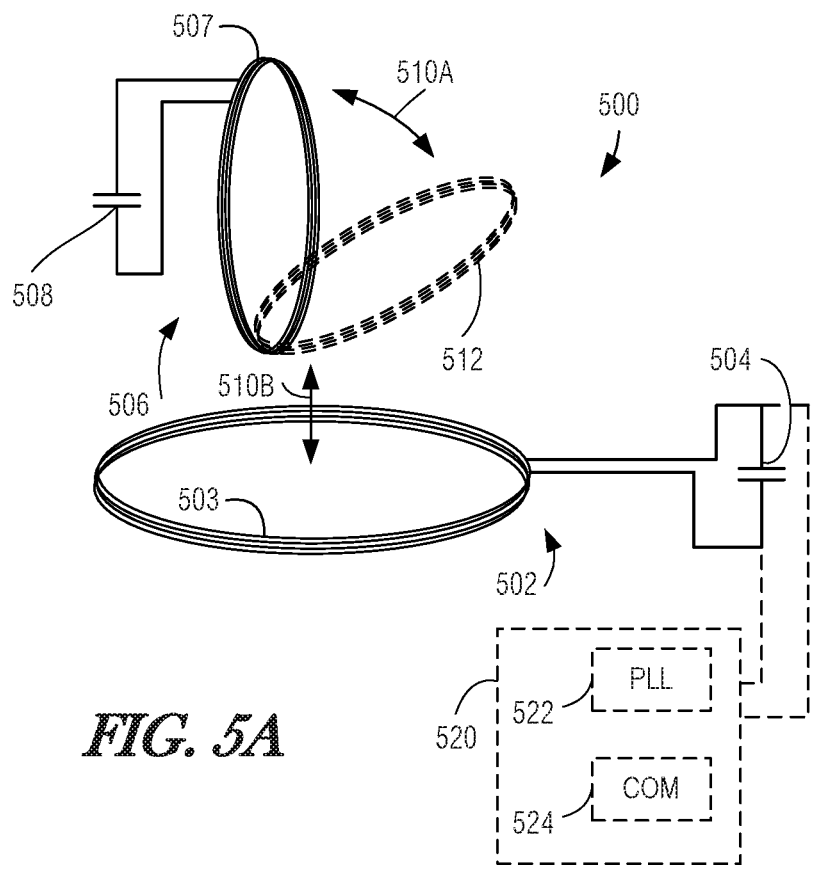
FIG. 5A is a diagram illustrating an example motion sensor according to some embodiments.

Another aspect of the invention is directed to a passive motion sensor that may be wirelessly read by a reader device. FIG. 5A is a diagram illustrating example motion sensor 500 according to some embodiments. Sensor 500 includes a first electrical resonator 502 and a second electrical resonator 506. First electrical resonator 502 and second electrical resonator 506 are each constructed as a coil of wire 503, 507 having an inductance L, in circuit with a capacitance C, indicated respectively at 504 and 508. The L-C circuits of each electrical resonator 502, 506 have a characteristic resonance that may be based on series or parallel L-C arrangements.

Electrical resonators 502 and 506 movably positionable relative to one another. For example, as depicted in FIG. 5A, second electrical resonator 506 is pivotable within range of motion 510A, and translatable along range of motion 510B.

First electrical resonator 502 and second electrical resonator 506 are configured to achieve resonant inductive coupling within at least a portion of the range of motion. The relative movement of the electrical resonators 502, 506 changes a detectable resonance property (e.g., resonance frequency) of the resonant inductive-coupled arrangement. Sensor 500 uses the principle of varying resonance characteristic in response to the relative motion of the electrical resonators 502, 506 to assess the relative motion of objects to which the electrical resonators 502, 506 are affixed.

In various embodiments, first electrical resonator 502 and second electrical resonator 506 are each constructed to exhibit a common resonance characteristic (e.g., resonance frequency, quality Q), even though their physical dimensions may differ. In other embodiments, the resonance characteristics of first electrical resonator 502 and second electrical resonator 506 may differ, though the relative positioning of the electrical resonators affect the overall resonance characteristics of sensor 500. In embodiments where the resonance characteristic is common to both first electrical resonator 502 and second electrical resonator 506, the sensing gain of sensor 500 is generally higher, and the output may be considered to be balanced, or differential, in nature.

Sensor 500 may be read by coupling an excitation signal to at least one of the electrical resonators 502, 506, and measuring an electrical characteristic of the excitation signal in response to the varying resonance characteristic due to the relative movement of the electrical resonators.

For example, the excitation signal may have a carrier frequency that matches a resonant frequency of sensor 500 (within the range of motion of electrical resonators 502, 506). When the electrical resonators are relatively positioned to tune sensor 500 to be resonant at the carrier frequency of the excitation signal, the loading of excitation signal is minimized. As the relative movement of electrical resonators 502, 506 de-tunes the resonant frequency of sensor 500 from the frequency of the excitation signal, the loading of the excitation signal would tend to increase. Accordingly, the source or coupling of the excitation signal can monitor the voltage, current, or other electrical parameter, such as reflected RF power, for example, to assess the relative movement of the electrical resonators.

In another example, the generator of the excitation signal may continuously adjust the frequency of the carrier frequency to match the resonance frequency of sensor 500 using a feedback control system such as a phase-locked loop (PLL). The error or control signal of the control system may be used as the output of the movement detector.

In one embodiment, the excitation signal is wirelessly coupled to the first electrical resonator by a remote excitation signal generator. The remote excitation signal generator may be incorporated as part of a RFID reader according to one embodiment. This approach advantageously utilizes sensor 500 as an entirely passive sensor that may be read wirelessly from a remotely-located (i.e., in spaced relationship) reader. In this type of embodiment, the excitation signal may be a RFID interrogation signal.

In another embodiment, as depicted using the dashed lines in FIG. 5A, the excitation signal may be generated locally by an excitation circuit 520. Excitation circuit includes a signal generator and, in some embodiments, a PLL 522 for adjusting the frequency of the excitation signal to match the resonance characteristic of sensor 500 as it changes due to the relative motion of electrical resonators 502, 506.

In a related embodiment, sensor 500 is electrically coupled to a signal communicator 524 that is configured to modulate the electrical characteristics of sensor 500 in a manner that affects the loading, voltage-current phase offset angle, or resonance frequency as seen by the excitation signal. For instance, communicator 524 may include a transistor configured to adjust the impedance of sensor 500 in response to a signal input. In another embodiment, communicator may include an electrically-variable capacitor that adjusts the resonant frequency of sensor 500. A combination of impedance and resonance adjustment is also contemplated in related embodiments. Communicator 524 main overlay certain information on the carrier frequency, such as a sensor ID number, or other measured parameter, such as ambient temperature, accelerometer reading, magnetometer reading, or the like, from a secondary sensor incorporated with sensor 500.

In another related embodiment, sensor 500 includes a RFID tag that uses at least one of coils 503, 507 as its antenna. The RFID tag may be a passive RFID tag that captures, and utilizes, energy from a RFID interrogation signal. The RFID interrogation signal may also serve as the excitation signal for reading sensor 500.

Figure 5B:
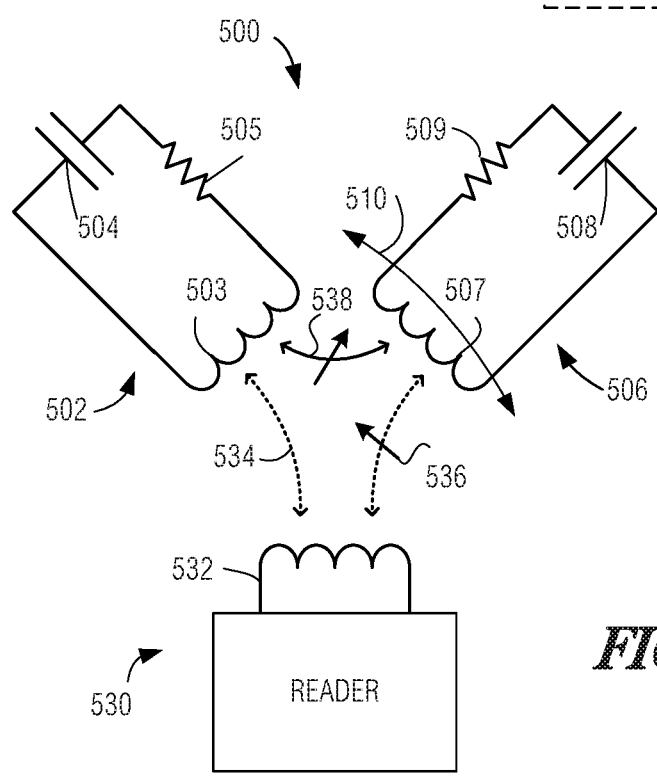
FIG. 5B is a schematic diagram illustrating an electrical relationship when the example motion sensor of FIG. 5A is being read by reader.

FIG. 5B is a schematic diagram illustrating an electrical relationship when sensor 500 is being read by reader 530. Each of the electrical resonators 502, 506 is modeled as a RLC circuit with the inclusion of lumped-parameter resistors 505 and 509 to represent the distributed resistance in coils 503 and 507, and in capacitors 504 and 508. Electrical resonators 502 and 506 experience a variable resonant inductive coupling 538, which varies based on the relative positioning of the electrical resonators 502, 506. In this example, electrical resonator 502 is maintained generally stationary, while electrical resonator 506 is movable according to range of motion 510.

Reader 530 includes a coil 532 and other circuitry to excite electrical resonators 502, 506. In a related embodiment, reader 530, including coil 532 and associated circuitry (not shown) match a resonance characteristic of resonators 502 and 506. When reader 530 is brought into proximity with electrical resonators 502 and 506, a resonant inductive coupling 534 is established with resonator 502, and a variable resonant inductive coupling 536 is established with resonator 506. Resonant inductive couplings 534 and 536 are generally much weaker than resonant inductive coupling 538 between coils 503 and 507 of sensor 500; thus, the effect on the resonance characteristics of sensor 500 due to the presence of reader 530 is negligible in such embodiments. Movement of electrical resonator 506 relative to electrical resonator 502 is the primary mechanism that varies the resonance characteristic of the system, which reader 530 is configured to drive, and detect.

FIGS. 6A and 6B are diagrams illustrating an example application of a passive motion sensor, such as sensor 500, to monitor the operation of an artificial heart valve according to an illustrative embodiment. Reference numerals 600A and 600B refer to the same valve in different states. The valve is generally referred to as valve 600. It includes a valve body 602 that forms a periphery defining a passage. A pair of occluders, such as flaps, 604 and 606, are movable between a closed position, as depicted at 604A and 606A in FIG. 6A, and an open position depicted in FIG. 6B at 604B and 606B. The range of motion of each occluder 604, 606 is depicted with the dashed arrows in FIG. 6B.

A first electrical resonator 610 is fixed to the valve body 602. Second and third electrical resonators 612 and 614 are affixed respectively to occluders 604 and 606. The first electrical resonator 610 and each one of the second electrical resonator 612 and third electrical resonator 614 are configured to achieve resonant inductive coupling within at least a portion of the range of motion of second and third electrical resonators 612, 614. The resonant inductive coupling is resonant with a carrier frequency of an excitation signal (not shown) coupled to at least the first electrical resonator 610.

A change in relative positioning of the first electrical resonator 610 and the second and third electrical resonators 612, 614 resulting from relative motion of the valve body 602 and the occluders 604, 606 causes a change in a detectable resonance property of the electrical resonator arrangement of the motion sensor. The excitation signal may be provided by a distinct reader device, such as a RFID reader, for example.

FIG. 7 is a diagram illustrating another example application for a passive sensor, such as sensor 500, where the sensor is incorporated with a diaphragm 702. The diaphragm 702 may be affixed to a blood vessel such as an artery, aorta, or an organ of a patient, to detect the patient's pulse. In some embodiments, the pulse pressure may be measured as well. In diaphragm 702, the center undergoes greater displacement than the edge. Accordingly, a first coil 710 is situated at or near the edge of the diaphragm, and a second coil 712 is situated closer to the center of the diaphragm. First coil 710 may be on the diaphragm itself (as depicted in FIG. 7), or at the base of the diaphragm (not shown). Coils 710 and 712 may be concentrically arranged, as depicted, or they may be center-offset, according to various embodiments. Movement of the diaphragm causes a change in the resonance characteristics of the inductive resonant-coupled coils, which may be detected using one or more of the techniques described herein.

Figure 8:
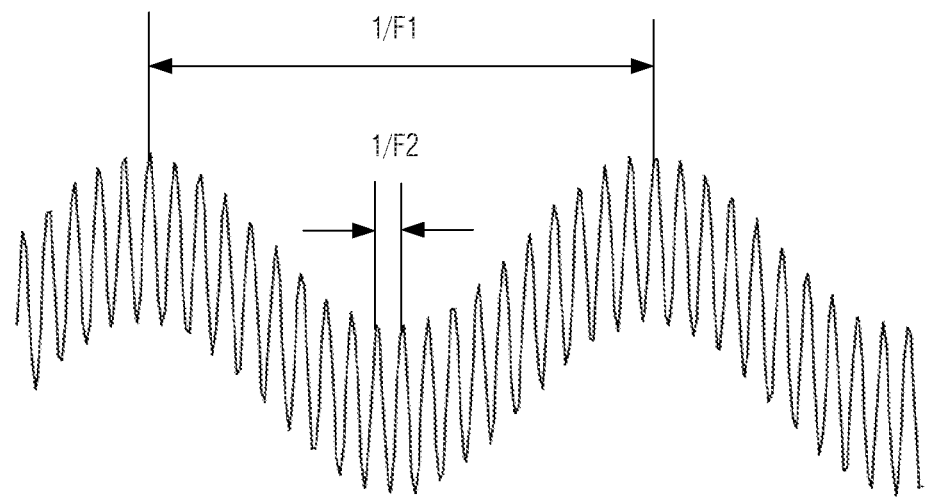
FIG. 8 is a signal diagram illustrating an output of a motion sensor according to an embodiment.

FIG. 8 is a signal diagram illustrating an output of a motion sensor such as motion sensor 500 according to an embodiment in which motion sensor 500 includes communicator 524. The signal depicted may be a current or a voltage of an excitation signal coupled to sensor 500 by an external reader. The signal shown in FIG. 8 appears as a summation of a low-frequency signal having a period of 1/F1, where F1 is a nominal frequency of the low-frequency signal, and a high-frequency signal having a period of 1/F2, where F2 is a nominal frequency of the high-frequency signal. The low-frequency signal represents relative movement of the electrical resonators and is produced according to the principle of varying resonance characteristic as described above. The high-frequency signal in this example represents a subcarrier wave that may be generated by communicator 524 and further modulated to encode information, such as an ID of sensor 500, for instance. Notably, the signal depicted in FIG. 8 represents the baseband signal recovered from the RF carrier frequency used for the excitation signal, such as an RFID interrogation signal, for instance.

Figure 9:
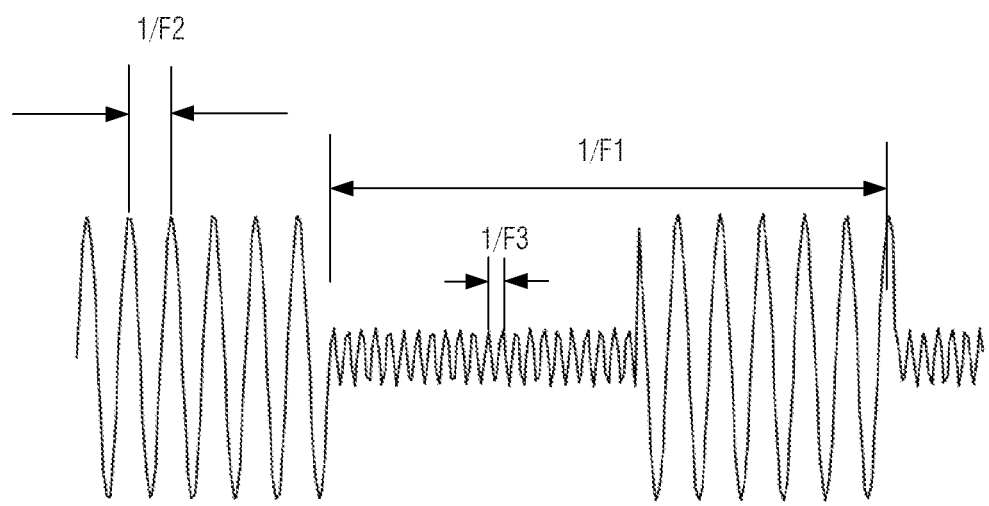
FIG. 9 is a diagram illustrating another type of output of a motion sensor according to an embodiment.

FIG. 9 is a diagram illustrating an output of a motion sensor such as motion sensor 500 in an embodiment in which the excitation signal is adjusted to track the current resonant frequency of motion sensor 500. In this example, three distinct frequencies are depicted. Frequency F1 represents the movement-based modulation of the carrier signal. Frequencies F2 and F3 represent the carrier signal at different states of motion sensor 500. When the relative positioning of the electrical resonators is in a first state, F2 is the resonant frequency; when the relative positioning of the electrical resonators is in a second state, F3 is the resonant frequency. Also evident from this example is that the load experienced by the excitation signal may vary depending on the extent of resonant inductive coupling of the resonators of sensor 500, as represented in the different amplitudes of the signal shown in FIG. 9. Accordingly, the monitored movement may be assessed using amplitude analysis, spectral analysis, or both.

ADDITIONAL NOTES & EXAMPLES

Example 1 is a biomedical implant for implantation inside a patient comprising: a wall enclosing at least a portion of the implant, the wall including: a first stratum; a second stratum conformal with the first stratum; an interlayer between the first and the second strata, the interlayer including a structure that produces capillary pressure in an infiltrating fluid in response to rupture of at least one of the first stratum and the second stratum resulting in entry of the infiltrating fluid into the interlayer; a detector exposed to the interlayer, the detector configured to detect a presence, if any, of the infiltrating fluid and output a detection state indicator; and a communication circuit communicatively coupled to the detector and configured to communicate the detection state indicator to a reader external to the patient.

In Example 2, the subject matter of Example 1 optionally includes wherein the wall is an exterior wall of the implant.

In Example 3, the subject matter of any one or more of Examples 1-2 optionally include wherein the wall is formed from a flexible material.

In Example 4, the subject matter of any one or more of Examples 1-3 optionally include wherein the interlayer includes a plurality of microfluidic channels fluidly coupled to the detector.

In Example 5, the subject matter of any one or more of Examples 1-4 optionally include wherein the interlayer includes an absorbent material fluidly coupled to the detector.

In Example 6, the subject matter of any one or more of Examples 1-5 optionally include wherein the first stratum has an outside-facing first surface interfaced with an inside-facing second surface of the second stratum, and wherein at least one of the first surface and the second surface includes a surface texture that forms capillary structures within the interlayer.

In Example 7, the subject matter of any one or more of Examples 1-6 optionally include wherein the detector is incorporated in a radio-frequency identification (RFID) tag situated in the interlayer.

In Example 8, the subject matter of Example 7 optionally includes wherein the communication circuit is a passive RFID circuit configured to capture energy from an interrogation signal; and wherein the RFID tag is configured to also capture energy from the interrogation signal and to utilize that captured energy to operate the detector to communicate data obtained by operation of the detector to the communication circuit.

In Example 9, the subject matter of any one or more of Examples 1-8 optionally include a data collector device configured for implantation inside the patient, the data collector device being configured to wirelessly receive data from the communication circuit and to transmit the data to a reader device situated on the exterior of the patient.

In Example 10, the subject matter of Example 9 optionally includes wherein the data collector device includes a passive RFID circuit configured to capture energy from an interrogation signal and to use the captured energy to wirelessly receive the data from the communication circuit and to transmit the data to the reader device.

In Example 11, the subject matter of any one or more of Examples 9-10 optionally include wherein the data collector device includes a non-volatile memory device configured to store at least a portion of the data.

In Example 12, the subject matter of any one or more of Examples 1-11 optionally include a sensor system that includes: a first tag including the detector and the communication circuit; and a second tag including a second communication circuit; wherein the first tag and the second tag are configured such that, in operation: the first tag is to initiate a first wireless transmission for reception by the second tag, the wireless transmission pertaining to a measurement effected by the detector; and the second tag is to wirelessly communicate data representing the measurement to a reader device.

In Example 13, the subject matter of Example 12 optionally includes wherein the first wireless transmission includes data representing the measurement.

In Example 14, the subject matter of Example 13 optionally includes wherein the second tag is a collector tag configured to store the data representing the measurement and to incorporate the data into a second wireless transmission for reception by the reader.

In Example 15, the subject matter of Example 14 optionally includes wherein the first wireless transmission is in a first radio-frequency band, and wherein the second wireless transmission is in a second radio-frequency band that is different from the first radio-frequency band.

In Example 16, the subject matter of any one or more of Examples 12-15 optionally include wherein the second tag is to store a plurality of measurements including said measurement.

In Example 17, the subject matter of Example 16 optionally includes wherein the second tag is to aggregate the plurality of measurements into an aggregated set, wherein the aggregated set represents said measurement, and wherein the second tag is to communicate the aggregated set to the reader device.

In Example 18, the subject matter of any one or more of Examples 12-17 optionally include wherein the first tag and the second tag are operatively arranged in a spaced relationship.

Example 19 is a passive motion sensor, comprising: a first electrical resonator and a second electrical resonator; wherein the first electrical resonator and the second electrical resonator are movably positionable relative to one another within a range of motion; and wherein the first electrical resonator and the second electrical resonator are configured to achieve resonant inductive coupling within at least a portion of the range of motion, the resonant inductive coupling being resonant with a carrier frequency of an excitation signal coupled to at least the first electrical resonator; wherein a change in relative positioning of the first electrical resonator and the second electrical resonator causes a change in a detectable resonance property of the motion sensor.

In Example 20, the subject matter of Example 19 optionally includes wherein the excitation signal is wirelessly coupled to the first electrical resonator by a remote excitation signal generator.

In Example 21, the subject matter of Example 20 optionally includes wherein the excitation signal is a radio frequency identification (RFID) interrogation signal.

In Example 22, the subject matter of any one or more of Examples 20-21 optionally include a communicator circuit configured to send a data stream using a modulation of electrical characteristic of at least one of the first and second electrical resonators.

In Example 23, the subject matter of any one or more of Examples 19-22 optionally include wherein the excitation signal is conductively coupled to the first electrical resonator by a local excitation signal generator.

In Example 24, the subject matter of any one or more of Examples 19-23 optionally include wherein the first electrical resonator and the second electrical resonator are pivotally movable relative to one another.

In Example 25, the subject matter of any one or more of Examples 19-24 optionally include wherein the first electrical resonator and the second electrical resonator are translationally movable relative to one another.

In Example 26, the subject matter of any one or more of Examples 19-25 optionally include wherein the first electrical resonator and the second electrical resonator each includes a coil and a capacitor electrically coupled to the coil.

In Example 27, the subject matter of any one or more of Examples 19-26 optionally include wherein the detectable resonance property includes a loading of a generator of the excitation signal.

In Example 28, the subject matter of any one or more of Examples 19-27 optionally include wherein the detectable resonance property includes a resonant frequency of the resonant inductive coupling, and wherein the excitation signal is controlled such that the carrier frequency tracks the resonant frequency of the resonant inductive coupling.

Example 29 is a valve, comprising: a valve body forming a periphery defining a passage; an occluder movably coupled to the valve body and movable within a range of motion; a first electrical resonator fixed to the valve body; and a second electrical resonator fixed to the occluder; wherein the first electrical resonator and the second electrical resonator are configured to achieve resonant inductive coupling within at least a portion of the range of motion, the resonant inductive coupling being resonant with a carrier frequency of an excitation signal coupled to at least the first electrical resonator; wherein a change in relative positioning of the first electrical resonator and the second electrical resonator resulting from relative motion of the valve body and the occluder causes a change in a detectable resonance property of the motion sensor.

In Example 30, the subject matter of Example 29 optionally includes wherein the valve is an artificial heart valve.

In Example 31, the subject matter of any one or more of Examples 29-30 optionally include wherein the excitation signal is wirelessly coupled to the first electrical resonator by a remote excitation signal generator.

In Example 32, the subject matter of Example 31 optionally includes wherein the excitation signal is a radio frequency identification (RFID) interrogation signal.

In Example 33, the subject matter of any one or more of Examples 29-32 optionally include a communicator circuit configured to send a data stream using a modulation of electrical characteristic of at least one of the first and second electrical resonators.

In Example 34, the subject matter of any one or more of Examples 29-33 optionally include wherein the excitation signal is conductively coupled to the first electrical resonator by a local excitation signal generator.

In Example 35, the subject matter of any one or more of Examples 29-34 optionally include wherein the first electrical resonator and the second electrical resonator are pivotally movable relative to one another.

In Example 36, the subject matter of any one or more of Examples 29-35 optionally include wherein the first electrical resonator and the second electrical resonator are translationally movable relative to one another.

In Example 37, the subject matter of any one or more of Examples 29-36 optionally include wherein the first electrical resonator and the second electrical resonator each includes a coil and a capacitor electrically coupled to the coil.

In Example 38, the subject matter of any one or more of Examples 29-37 optionally include wherein the detectable resonance property includes a loading of a generator of the excitation signal.

In Example 39, the subject matter of any one or more of Examples 29-38 optionally include wherein the detectable resonance property includes a resonant frequency of the resonant inductive coupling, and wherein the excitation signal is controlled such that the carrier frequency tracks the resonant frequency of the resonant inductive coupling.

Example 40 is a sensor system, comprising: a first tag including a first communication circuit, and a first encapsulation structure enclosing the first communication circuit; and a second tag including a second communication circuit and a second encapsulation structure enclosing the second communication circuit; wherein the first tag and the second tag are configured such that, in operation: the first tag is to initiate a first wireless transmission for reception by the second tag, the wireless transmission pertaining to a measurement effected by the first tag or the second tag; and the second tag is to wirelessly communicate data representing the measurement to a reader device.

In Example 41, the subject matter of Example 40 optionally includes wherein the first tag comprises a detector tag that comprises a sensing transducer circuit configured to take measurements of an environment surrounding the detector tag, and wherein the first wireless transmission includes data representing the measurement.

In Example 42, the subject matter of Example 41 optionally includes wherein the second tag is a collector tag configured to store the data representing the measurement and to incorporate the data into a second wireless transmission for reception by the reader.

In Example 43, the subject matter of Example 42 optionally includes wherein the first wireless transmission is in a first radio-frequency band, and wherein the second wireless transmission is in a second radio-frequency band that is different from the first radio-frequency band.

In Example 44, the subject matter of any one or more of Examples 42-43 optionally include wherein the first tag and the second tag are each adapted for implantation inside an animal, and wherein second wireless transmission is a transcutaneous signal.

In Example 45, the subject matter of Examples 40 optionally includes wherein the first wireless transmission by the first tag is a sense-stimulation signal, and wherein the second tag is to measure a signal property of the sense-stimulation signal to take the measurement.

In Example 46, the subject matter of Example 45 optionally includes wherein the sense-stimulation signal includes a first frequency component and a second frequency component, and wherein the signal property measured by the second tag includes a change in relative signal strength between the first frequency component and the second frequency component.

In Example 47, the subject matter of any one or more of Examples 40-46 optionally include wherein the second tag is to store a plurality of measurements including said measurement.

In Example 48, the subject matter of Example 47 optionally includes wherein the second tag is to aggregate the plurality of measurements into an aggregated set, wherein the aggregated set represents said measurement, and wherein the second tag is to communicate the aggregated set to the reader device.

In Example 49, the subject matter of any one or more of Examples 40-48 optionally include wherein the first tag and the second tag are operatively arranged in a spaced relationship.

In Example 50, the subject matter of any one or more of Examples 40-49 optionally include wherein the first tag is configured such that, in operation, the first tag is to store energy from a wireless interrogation signal transmitted by a reader device and to utilize the stored energy to effect operation of the first tag.

In Example 51, the subject matter of Example 50 optionally includes wherein the second tag is also configured such that, in operation, the second tag is to store energy from the wireless interrogation signal transmitted by a reader device and to utilize that stored energy to effect operation of the second tag.

In Example 52, the subject matter of any one or more of Examples 40-51 optionally include a biomedical implant for implantation inside a patient, the biomedical implant comprising: a wall enclosing at least a portion of the implant, the wall including: a first stratum; a second stratum conformal with the first stratum; and an interlayer between the first and the second strata, the interlayer including a structure that produces capillary pressure in an infiltrating fluid in response to rupture of at least one of the first stratum and the second stratum resulting in entry of the infiltrating fluid into the interlayer; wherein the first tag comprises a detector exposed to the interlayer, the detector configured to detect a presence, if any, of the infiltrating fluid and output a detection state indicator.

In Example 53, the subject matter of Example 52 optionally includes wherein the wall is an exterior wall of the implant.

In Example 54, the subject matter of any one or more of Examples 52-53 optionally include wherein the wall is formed from a flexible material.

In Example 55, the subject matter of any one or more of Examples 52-54 optionally include wherein the interlayer includes a plurality of microfluidic channels fluidly coupled to the detector.

In Example 56, the subject matter of any one or more of Examples 52-55 optionally include wherein the interlayer includes an absorbent material fluidly coupled to the detector.

In Example 57, the subject matter of any one or more of Examples 52-56 optionally include wherein the first stratum has an outside-facing first surface interfaced with an inside-facing second surface of the second stratum, and wherein at least one of the first surface and the second surface includes a surface texture that forms capillary structures within the interlayer.

In Example 58, the subject matter of any one or more of Examples 52-57 optionally include wherein the detector is incorporated in a radio-frequency identification (RFID) tag situated in the interlayer.

In Example 59, the subject matter of any one or more of Examples 40-58 optionally include a passive motion sensor that includes: a first electrical resonator and a second electrical resonator; wherein the first electrical resonator and the second electrical resonator are movably positionable relative to one another within a range of motion; and wherein the first electrical resonator and the second electrical resonator are configured to achieve resonant inductive coupling within at least a portion of the range of motion, the resonant inductive coupling being resonant with a carrier frequency of an excitation signal coupled to at least the first electrical resonator; wherein a change in relative positioning of the first electrical resonator and the second electrical resonator causes a change in a detectable resonance property of the motion sensor; and wherein at least one of the first or the second electrical resonator is electrically coupled to the first tag.

In Example 60, the subject matter of Example 59 optionally includes wherein the excitation signal is a radio frequency identification (RFID) interrogation signal.

In Example 61, the subject matter of any one or more of Examples 59-60 optionally include wherein the first tag is configured to send a data stream using a modulation of electrical characteristic of at least one of the first and second electrical resonators.

In Example 62, the subject matter of any one or more of Examples 59-61 optionally include wherein the excitation signal is conductively coupled to the first electrical resonator by a local excitation signal generator.

In Example 63, the subject matter of any one or more of Examples 59-62 optionally include wherein the first electrical resonator and the second electrical resonator are pivotally movable relative to one another.

In Example 64, the subject matter of any one or more of Examples 59-63 optionally include wherein the first electrical resonator and the second electrical resonator are translationally movable relative to one another.

In Example 65, the subject matter of any one or more of Examples 59-64 optionally include wherein the first electrical resonator and the second electrical resonator each includes a coil and a capacitor electrically coupled to the coil.

In Example 66, the subject matter of any one or more of Examples 59-65 optionally include wherein the detectable resonance property includes a loading of a generator of the excitation signal.

In Example 67, the subject matter of any one or more of Examples 59-66 optionally include wherein the detectable resonance property includes a resonant frequency of the resonant inductive coupling, and wherein the excitation signal is controlled such that the carrier frequency tracks the resonant frequency of the resonant inductive coupling.

Example 68 is a biomedical implant comprising the sensor system according to any one of Examples 40-51.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, also contemplated are examples that include the elements shown or described. Moreover, also contemplated are examples using any combination or permutation of those elements shown or described (or one or more aspects thereof), either with respect to a particular example (or one or more aspects thereof), or with respect to other examples (or one or more aspects thereof) shown or described herein.

Publications, patents, and patent documents referred to in this document are incorporated by reference herein in their entirety, as though individually incorporated by reference. In the event of inconsistent usages between this document and those documents so incorporated by reference, the usage in the incorporated reference(s) are supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to suggest a numerical order for their objects.

The above description is intended to be illustrative, and not restrictive. For example, the above-described examples (or one or more aspects thereof) may be used in combination with others. Other embodiments may be used, such as by one of ordinary skill in the art upon reviewing the above description. The Abstract is to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. However, the claims may not set forth every feature disclosed herein as embodiments may feature a subset of said features. Further, embodiments may include fewer features than those disclosed in a particular example Thus, the following claims are hereby incorporated into the Detailed Description, with a claim standing on its own as a separate embodiment. The scope of the embodiments disclosed herein is to be determined with reference to the appended claims, along with the full scope of equivalents to which such claims are entitled.

What is claimed is:

1. A biomedical implant for implantation inside a patient comprising:
a wall enclosing at least a portion of the implant, the wall including:
a first stratum;
a second stratum conformal with the first stratum;
an interlayer between the first and the second strata, the interlayer including a structure that produces capillary pressure in an infiltrating fluid in response to rupture of at least one of the first stratum and the second stratum resulting in entry of the infiltrating fluid into the interlayer; and
a sensor system that includes:
a first device including a detector and a first communication circuit, the detector being exposed to the interlayer, and including fluid-sensing circuitry to detect a presence, if any, of the infiltrating fluid, and the first communication circuit being operative to initiate a first wireless transmission containing a detection state indicator of the detector; and
a second device physically isolated from the first device, and including a second communication circuit interactive with the first device to receive the first wireless transmission, and to initiate a second wireless transmission to communicate the detection state indicator to a reader external to the patient.

2. The biomedical implant of claim 1, wherein the wall is an exterior wall of the implant.

3. The biomedical implant of claim 1, wherein the wall is formed from a flexible material.

4. The biomedical implant of claim 1, wherein the interlayer includes a plurality of microfluidic channels fluidly coupled to the detector.

5. The biomedical implant of claim 1, wherein the interlayer includes an absorbent material fluidly coupled to the detector.

6. The biomedical implant of claim 1, wherein the first stratum has an outside-facing first surface interfaced with an inside-facing second surface of the second stratum, and wherein at least one of the first surface and the second surface includes a surface texture that forms capillary structures within the interlayer.

7. The biomedical implant of claim 1, wherein the first device and the second device are each incorporated in a respective radio-frequency identification (RFID) tag, wherein the first device is situated in the interlayer.

8. The biomedical implant of claim 7, wherein the first communication circuit and the second communication circuit are each a passive RFID circuit configured to capture energy from an interrogation signal; and wherein the first device is operative to also capture energy from the interrogation signal to utilize that captured energy to operate the detector to communicate data obtained by operation of the detector to the first communication circuit.

9. The biomedical implant of claim 8, wherein the second communication circuit is to capture energy from the interrogation signal and to use the captured energy to wirelessly receive the data from the first communication circuit and to transmit the data to the reader.

10. The biomedical implant of claim 1, wherein the second device includes a non-volatile memory device configured to store the detection state indicator.

11. The biomedical implant of claim 1, wherein the first wireless transmission is in a first radio-frequency band, and wherein the second wireless transmission is in a second radio-frequency band that is different from the first radio-frequency band.

12. The biomedical implant of claim 1, wherein the second device is operative to aggregate a plurality of detection state indicators of the detector into an aggregated set, wherein the aggregated set, and wherein the second communication circuit is to communicate the aggregated set to the reader.

* * * * *